United States Patent [19]
Ostrow

[11] Patent Number: 5,741,317
[45] Date of Patent: Apr. 21, 1998

[54] SUBMERSIVE THERAPY APPARATUS

[75] Inventor: Alvin Stewart Ostrow, Raanana, Israel

[73] Assignee: Electromagnetic Bracing Systems, Ltd., Ra'anana, Israel

[21] Appl. No.: 665,092

[22] Filed: Jun. 14, 1996

[30] Foreign Application Priority Data

Jun. 15, 1995 [IL] Israel ................................ 114162

[51] Int. Cl.$^6$ .................................................... A61H 33/00
[52] U.S. Cl. ............................. 607/85; 607/81; 607/86
[58] Field of Search ....................... 607/80, 87, 97; 601/2; 604/20; 600/9–15

[56] References Cited

U.S. PATENT DOCUMENTS

| | | | |
|---|---|---|---|
| 2,570,081 | 10/1951 | Szczeniowski | 116/137 A |
| 2,970,073 | 1/1961 | Prange | 134/1 |
| 3,585,991 | 6/1971 | Balamath | 601/157 |
| 4,141,359 | 2/1979 | Jacobsen et al. | 604/20 |
| 5,042,479 | 8/1991 | Brotz | 607/87 |
| 5,048,520 | 9/1991 | Vago | 601/2 |
| 5,269,746 | 12/1993 | Jacobson | 600/13 |
| 5,339,804 | 8/1994 | Kemp | 601/2 |
| 5,344,384 | 9/1994 | Ostrow | 600/13 |

*Primary Examiner*—Jennifer Bahr
*Assistant Examiner*—David M. Ruddy
*Attorney, Agent, or Firm*—William Nitkin; Edward Langer

[57] ABSTRACT

A submersive therapy apparatus which includes a tub filled with an aqueous solution adapted to provide physiotherapy and drug treatment to the body or body parts of a patient, such as the hands, arms, feet or knees, such aqueous environment containing a medicated fluid and/or other liquid medium. An array of stationary ultrasonic acoustic transducers are arrayed within the walls of the tub which are connected to movable ultrasound heads. The ultrasound heads are exposed on the surface of the inner tub walls to concentrate ultrasound energy on a body part target area. Additionally and alternatively to the delivery of ultrasound energy, rows of electrodes and coils are arranged around all sides of the inner walls or panels of the tub in alternating positive or negative polarities to deliver an electric current and/or provide an electromagnetic field.

7 Claims, 4 Drawing Sheets

SUBMERSIVE THERAPY APPARATUS

BACKGROUND OF THE INVENTION

1. Field of the Invention

This invention resides generally in the field of medical appliances and more particularly relates to a medical appliance for the application of electrical and sound energy for therapeutic body treatment in a bath.

2. Description of the Prior Art

The use of phonophoresis and iontophoresis for drug delivery has been known and recognized as an acceptable form of treatment. Submersive therapy devices utilizing phonophoresis and magnetotherapy are found in the prior art.

Ultrasonic treatment devices are disclosed in U.S. Pat Nos. 3,585,991; 3,867,929; 5,042,479 and 5,339,804 having ultrasonic transducers which oscillate a liquid within a bath, but these devices do not provide for iontophoresis treatment. Among the previously discussed patents, "A Therapeutic Vibratory Bath" U.S. Pat No. 5,042,479 delivers selectable therapeutic treatment of acoustical, ultrasound or electromagnetic vibration protocols but also does not provide iontophoresis. U.S. Pat No. 5,344,384 discusses the uses of a "Magnetotherapy Apparaus" in combination with drug delivery but does not provide for submersive therapy.

Phonophoresis applications are found in the prior art, such as in U.S. Pat Nos. 4,767,402 and 5,016,615.

SUMMARY OF THE INVENTION

The device of this invention concerns an ultra-sound delivery apparatus incorporating multiple treatment modalities in a bath. The bath can be made of a heat, stain and shatter-resistant material such as plastic, fiberglass, Kevlar or equivalent material. The inner lining of the bath has multiple treatment heads around all sides and on the bottom of the tub basin to deliver ancillary optional treatment modalities including pulsed or continuous acoustic ultrasound and neuromuscular electrostimulation.

In addition to the application of sound energy in the present invention, a pulsed or continuous electric and electromagnetic field is created by a separate circuit. When a medicament is added to the aqueous environment, the invention becomes a drug delivery apparatus with a variety of protocols for phonophoretic, iontophoretic and electromagnetophoretic treatments.

In the submersive therapy apparatus of this invention the tub or tank surrounds the anatomical placement of the body or body part, such as a foot, arm, hand or knee, contained in an aqueous environment to administer ultrasound, pulsed electro-magnetic radiation or an electric field in connection with a liquid drug or aqueous medium.

The internal floor and/or walls of the submersive therapy apparatus tub are embedded with ultrasound heads, a plurality of electrodes, and magnetic coils that are focusable toward a body surface, enabling the submerging of a body or body part to obtain drug delivery and/or physiotherapy.

Furthermore, the ultrasound heads and electrode placement aims the delivery of acoustic ultrasound, electromagnetic radiation, and electrical current directionally at various angles and levels toward and around a targeted body part placed in the center of the bath. Delivery of submerged ultrasound therapy to a body part is known to be safe when given within a short distance from the ultrasound heads to avoid the danger of burning. When the liquid used in this apparatus is medicated, the ultrasound energy increases absorption of such drug through the skin.

An electrical current responsible for transdermal electrophoretic application can be simultaneously or singly used either for muscle stimulation or drug delivery treatment regimens. Alternating positive and negative currents can energize the electrodes.

The electromagnets that generate an electromagnetic signal in this invention are placed throughout the bath, providing a "checkerboard" pattern of magnetic fields that are cumulatively interactive.

A feature of this invention is that the electromagnetic therapy thereof provides deep magnetic flux penetration within a body part target area. Another aspect of this invention is the advantage of avoiding excessive heat transmitted to a target area from electromagnets by radiating an electromagnetic field through a fluid medium.

Yet another feature of this invention is the application of magnetic shielding built under and around the external surface of the tub to create a "rebound effect" which thereby increases the efficiency of the electromagnetic flux penetration within the body part target area.

Magnetotherapy, now well accepted for use in "bone growth stimulation" devices, has other therapeutic application. An "electromagnetophoresis phenomenon," supported by scientific research, exhibited that electromagnetic signals administered simultaneously in conjunction with drug delivery accelerates the metabolism of a drug medium in cellular tissues.

Another feature of this invention is the ability to provide auxiliary treatment to areas of the human body in a bath solution.

Electrophoresis and phonophoresis modalities treat mild to severe grades of foot, hand, elbow and knee disorders. These modalities, which are included in this apparatus, are beneficial for the rehabilitation of injuries and disorders such as "crush foot" syndrome, "carpal tunnel syndrome," "tennis elbow," "jumper's knee," "plantar fascitis," "tarsal tunnel syndrome" and a variety of traumatic, disease and infectious conditions of the upper and lower extremities of humans and animals. Individuals with severe traumatic conditions, such as those mentioned above, are often faced with the dilemma of chronic pain when conservative methods of surgery and physical therapy have failed.

Submersive phonophoresis is a method to replace conventional hand-held ultrasound devices which are cumbersome and physically time-consuming used to deliver physiotherapy. In submersive phonophoresis, a body part can easily "bathe" in a medicinal fluid and effortlessly receive a uniform radiation of acoustic ultrasonic energy and receive drugs transdermally in such medicinal fluid. Fingers and toes, for instance, are easier to treat in a submersive phonophoretic environment than current ultra-sound therapy methods used externally of a submersive bath.

In addition, as in the case of submersive phonophoresis methods mentioned above, it is an object of the present invention to deliver transdermal drug therapy with less effort in comparison to the norms of current day transdermal iontophoresis delivery devices available in the prior art.

Iontophoresis in a submersive bath eliminates iontophoretic burns associated with dermal electrodes, and therefore it is another object of the present invention to eliminate current-time compliance limitations associated with preventing burns with the use of dermal electrodes as they are not required with the present invention.

It is a still further object of this invention to provide an electromagnetic signal simultaneously with drug delivery to accelerate metabolism of a drug medium in human tissue so as to allow electromagnetophoresis treatment applications.

It is another object of this invention that the arrangement of the ultrasound heads and electrodes be consecutively positioned in a strategic manner to deploy an even continuity of acoustic sound, electromagnetic radiation, and electrical current energies throughout the bath solution.

It is yet a further object of the invention that a superior apparatus is made by increasing the effective absorption and acceleration of metabolism of drugs transported transdermally into a body target area with a uniform acoustic, electromagnetic and electrical field.

It is another object of this invention to provide a submersive therapy apparatus having selective curative regimens that can be applied singly or in combination.

A still further object of this invention is to provide a submersive therapy apparatus that is portable, comfortable to use, and cost effective to manufacture.

Additionally, it is an object of this invention that it be labor saving, whereby the ultrasound heads are made automatically movable by being motorized and controlled by a directional electronic switch so that the ultrasound heads can move in any angular or circular direction to deliver treatment without the need of hand labor to redirect such heads.

Furthermore, it is an object of this invention to create an apparatus using ultrasound, magnetotherapy and electrotherapy that is compatible with other commercialized units. The power used in the ultrasound application in the therapeutic bath of this invention oscillates a liquid in the power range of 1.0–3.0 watts per square centimeter of skin area, depending on the patient's tolerance and body target area to be treated.

The electrical current used in connection with the iontophoretic therapy component of this invention includes DC current modulation which can have trapezoid, square and sinusoidal wave pulses from 0–50 volts with alternating and continuous pulses modulated at between 1–200 hertz and electrical current ranging from 0–50 mA, with a current range from 0–15 mA. For electrophoresis, the mode can vary 50% "on", 50% "off" or as desired. For neuromuscular stimulation, the pulses have a 20% to 30% "off" and 70% to 80% "on" timing for maximum effectiveness. In this regard, the electrical muscle stimulation can be effected concurrently with, or independently of, the iontophoretic therapy.

The magnetotherapy aspect of this invention uses pulsed or continuous electromagnetic frequency signals ranging from 0–100 hertz.

In addition to the commercial units available in the art that can be compatible with the apparatus, it is a further object that an accessory console be provided to make the apparatus of this invention adaptable to have the ability to receive male and female electrode jacks from other available devices used in the art of ultrasound therapy, electrotherapy and magnetotherapy.

It should be apparent that the multi-modal nature of this apparatus covers a broad spectrum of treatment protocols, including treatment of injuries to soft and hard tissue structures, that may be applied at selected locations on the human body.

In view of the foregoing, it should be apparent that the present invention overcomes many of the shortcomings and disadvantages of the prior art and provides an improved apparatus.

DESCRIPTION OF THE PREFERRED EMBODIMENT(S)

Figure 1:
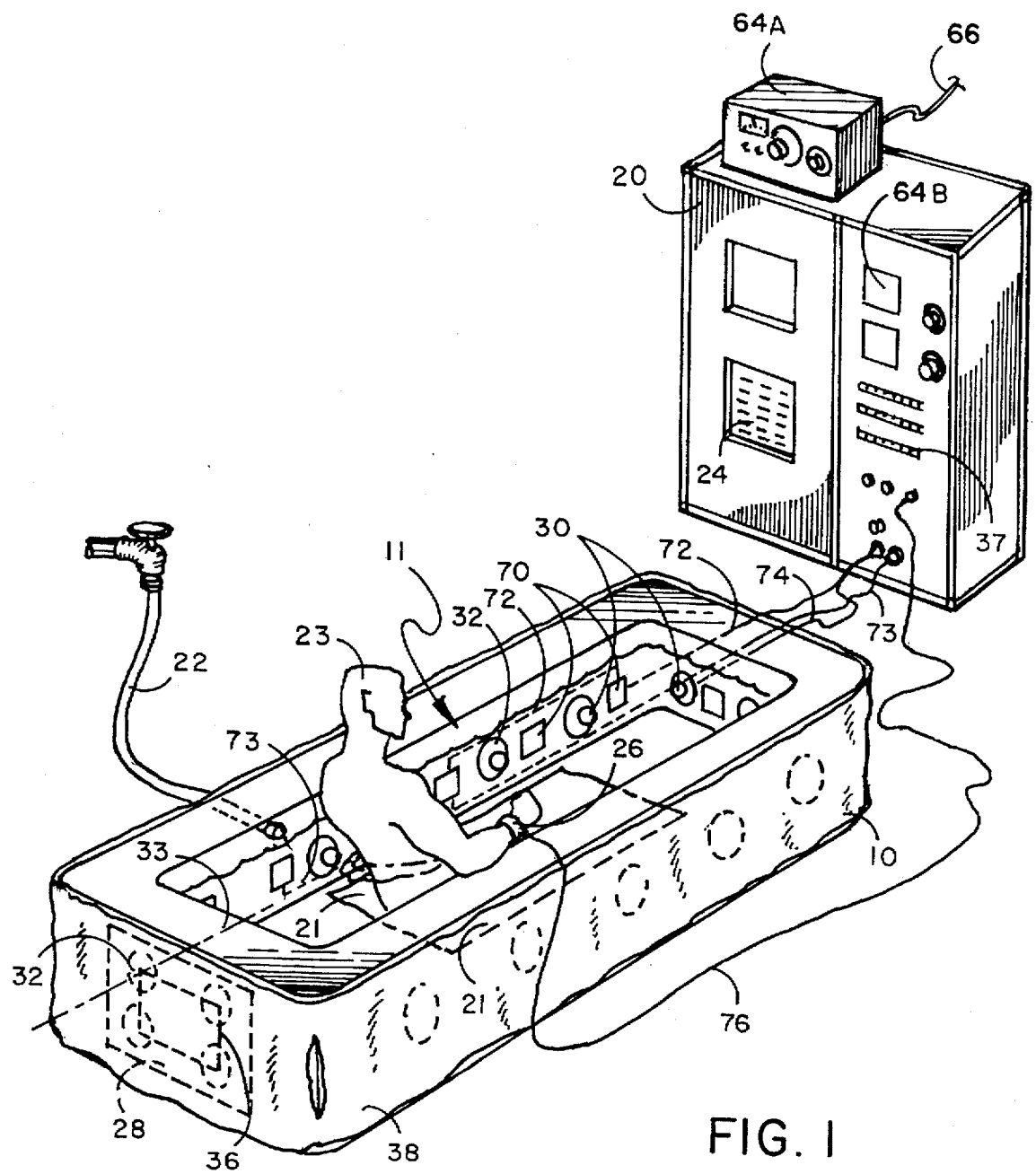
FIG. 1 illustrates a perspective view of one embodiment of the device of this invention showing a console, a tub with ultrasound head, magnetic coil and electrode placements around the inner surface of the tub with a patient in the tub.

FIG. 1 illustrates a perspective representation of portable submersive therapy tub 10 which has a tank portion adequate for the anatomical placement of a patient 23 or body part such as a foot, arm, hand or knee to administer therapy thereto in a fluid medium.

Figure 2:
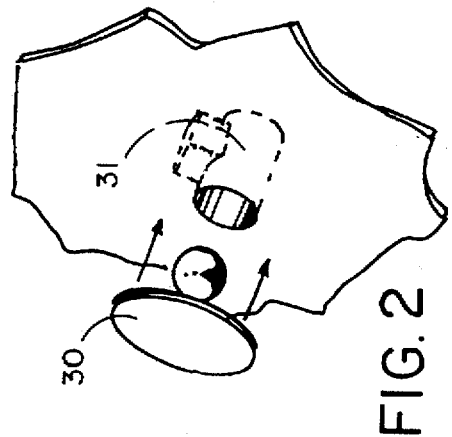
FIG. 2 illustrates a perspective view of a housing for an ultrasound head shown separated from its housing.

An array of multiple treatment ultrasound heads 30, seen in FIGS. 1 and 2, can be composed of a silver, gold, stainless steel or similar alloy are seen disposed around the side panels of the tub and can be on the bottom of the tub facing the anatomical target area 11 holding the body or body part to be treated. The ultrasound heads 30 are housed in socketball type joint housing 31 to allow rotational movement of the heads while the location for each joint housing of the ultrasound transducers remains fixed in the tub. Ultrasound heads 30 can be motorized and movable by a directional electronic switch 37 seen on console 20 so as to move any selected head in any desired angular direction.

The apparatus seen in FIG. 1 is energized by and from an external power source through a portable or stationary console 20 showing the menu of options 24 of single or of a combination of electrotherapeutic modalities and also for delivery for submersive form of a metalized or composite material forming a substrate 38 of a mesh or composite material within the outer surface of the plastic, fiberglass or Kevlar tub. Substrate 38 prevents "leakage" of the electromagnetic field and creates a rebound effect, increasing the effectiveness of the magnetic field.

Figure 3:
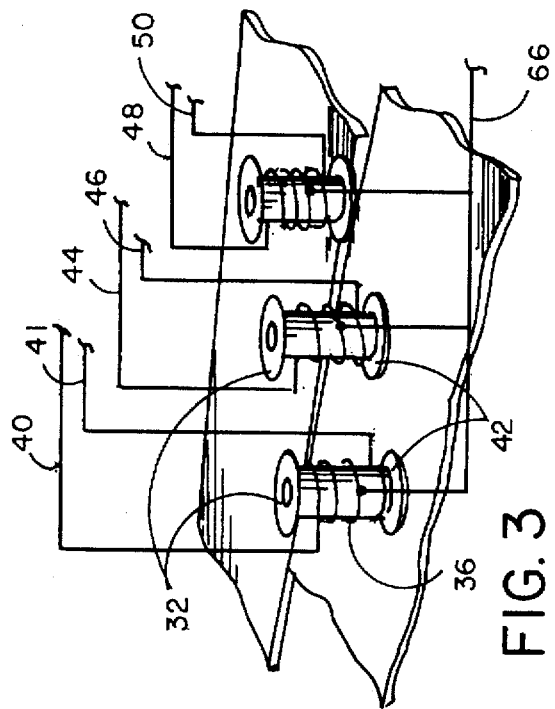
FIG. 3 illustrates a perspective view of cores used in the fabrication of each magnetic coil which is wrapped with helical conductive windings and showing the electrical circuitry for energizing the magnetic coils.
Figure 4:
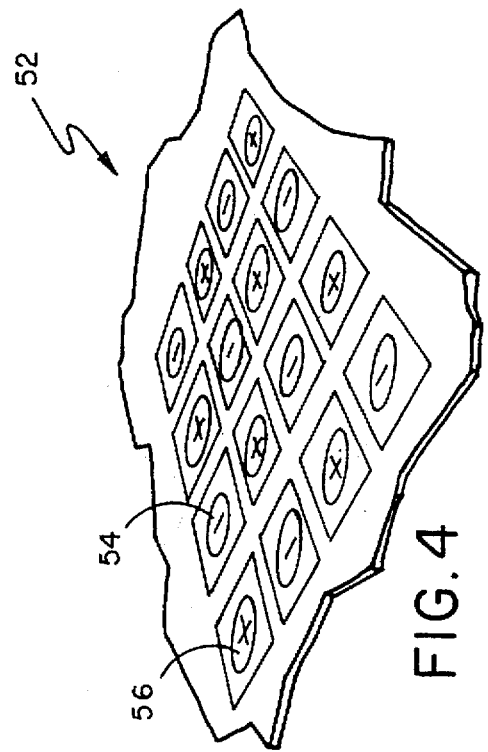
FIG. 4 illustrates a perspective view of one embodiment of a panel placed on the tub surface showing diagrammatically the "checkerboard" pattern of the magnetic coils and their corresponding polarities.

Referring now to coil 42 seen in FIG. 3, it will be noted that the wiring sequence around each core 32 can provide for a current flow through adjacent magnetic coils 42 in opposite directions to thereby generate a "checkerboard" of magnetic fields of alternate polarities as graphically depicted in FIG. 4. This current flow is accomplished by conductively coupling the windings of coils 42 in two circuits as will be further described below.

Figure 5:
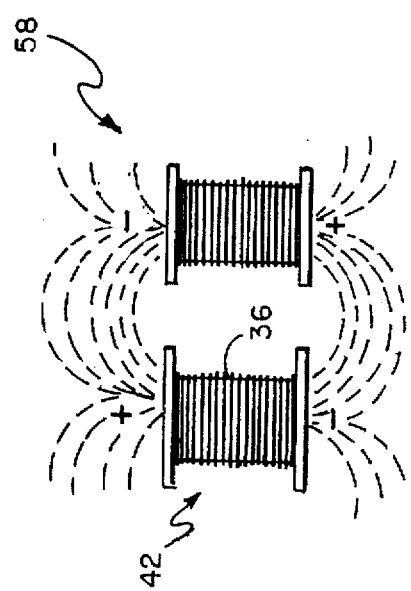
FIG. 5 illustrates a side view of adjacent magnetic coils, showing the combined lines of induction radiating from adjacent magnetic coils of opposite polarity.

In an isolated sectional view of FIG. 5 two adjacent coils 42 produce magnetic lines of induction 58. The direction of the induction vector is indicated by the arrow heads on each of the lines of induction 58. It will thereby be observed that the cooperative interaction of the magnetic fields of similar polarity will provide a greater magnitude of magnetic flux and concurrently a deeper local penetration into muscle and bone tissue.

The preferred power supply of this invention is a wall outlet attached to console 20. With reference to FIG. 1, in one embodiment two pulse signal generators 64a and 64b can be included within console 20. Pulse signal generator 64a supplies a.c. power for the electromagnetic field therapy, and the other pulse signal generator 64b supplies d.c. power for electrostimulation and electrophoretic pharmaceutical delivery, both of which will be described below.

With regard to the electromagnetic field therapy, a computerized chip distribution system monitors and supplies the strongest current directly to coils 42 positioned over the target area according to a treatment protocol. A weaker current will be supplied to the second anatomical structure surrounding the target area. This is an optional feature which is built into the console.

Figure 7:
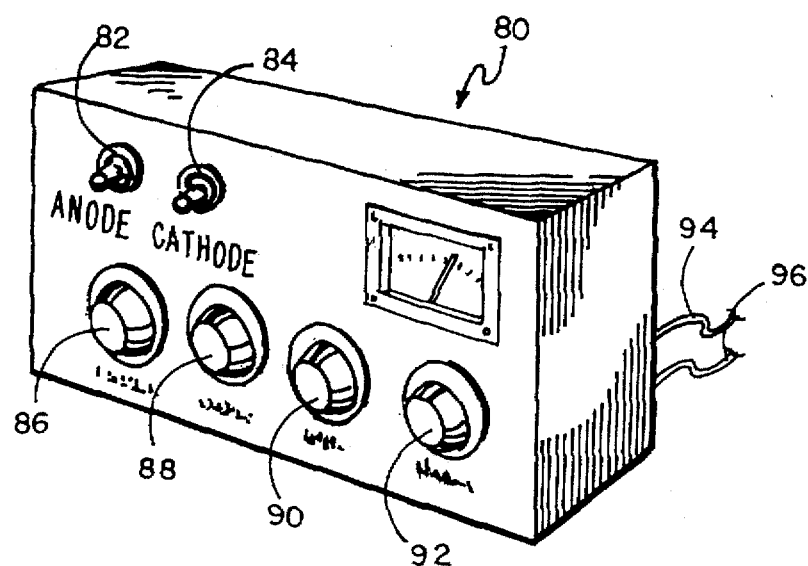
FIG. 7 illustrates a perspective view of an adaptable console that can be used with other model ultra-sound and electrotherapy units.

Referring once again to pulse signal generator 64a, an asymmetrical trapezoidal waveform having approximately a 15%–16% greater negative value than positive value is fed to magnetic treatment coils 42. For this purpose a wire harness 74 is conductively coupled to the console connection leading to the tub by a set of three-conductor connector plugs that are accommodatingly received within a corresponding set of sockets. Referring to FIG. 3, it will be seen that the three electric conductor lines, such as 40, 41 and 66, respectively, complete two independent circuits for energizing alternating treatment coils 42. Each coil 42 can thus be independently controlled as to magnetic field intensity and direction of its magnetic polarity. It will be noted that when the current flows in a clockwise direction through the windings in treatment coils 42 in one circuit using electric lines 40 and 66, the current will correspondingly flow in counterclockwise direction throughout the windings of treatment coils 42 within the other circuit using electric lines 41 and 66. The pulsed trapezoid and/or rectangular or square waveform can have a periodic frequency within the range of 1–100 hertz and is preferably not more than 16 hertz when used for electromagnetic therapy. The preferred range of magnetic flux density should not exceed 100 gauss. FIG. 7 illustrates a perspective view of an independent pulse signal generator 80 which can be used to attach by electrical line 94 and 96 to the tub controlled by switches 82 and 84 and knobs 86, 88, 90 and 92 to perform similar functions to those of console 20.

The magnetotherapy apparatus of this invention can best be utilized for inducing an electromagnetic field into the human body extradermally and can simultaneously treat open and closed wounds and trauma in a bath solution.

Further, with regard to the additional treatment modalities, the electrostimulation component provides galvanic muscle stimulation for producing muscle contractions that deter the onset of atrophy in an immobilized body part. This electrostimulation regimen is also effective for reversing the degenerative effect of atrophia.

This aspect of the invention includes the incorporation of a set of rows of conductive stimulator electrodes 70, seen in FIG. 1. Stimulator electrodes 70 are housed and applied in the plastic or similar materialized modular surface to be exposed throughout the inner bathing surface of the tub to have electrodes 70 in contact with an aqueous solution. Line conductors 72 and 73 provide their respective electrodes 70 with opposite charges of d.c. current. When patient 23 is placed within tub 10, stimulator electrodes 70 are in direct contact with an aqueous solution to transfer and conduct electrostimulation to the skin surface.

The previously described muscular stimulation can be used independently or in combination with electromagnetic therapy.

Figure 8:
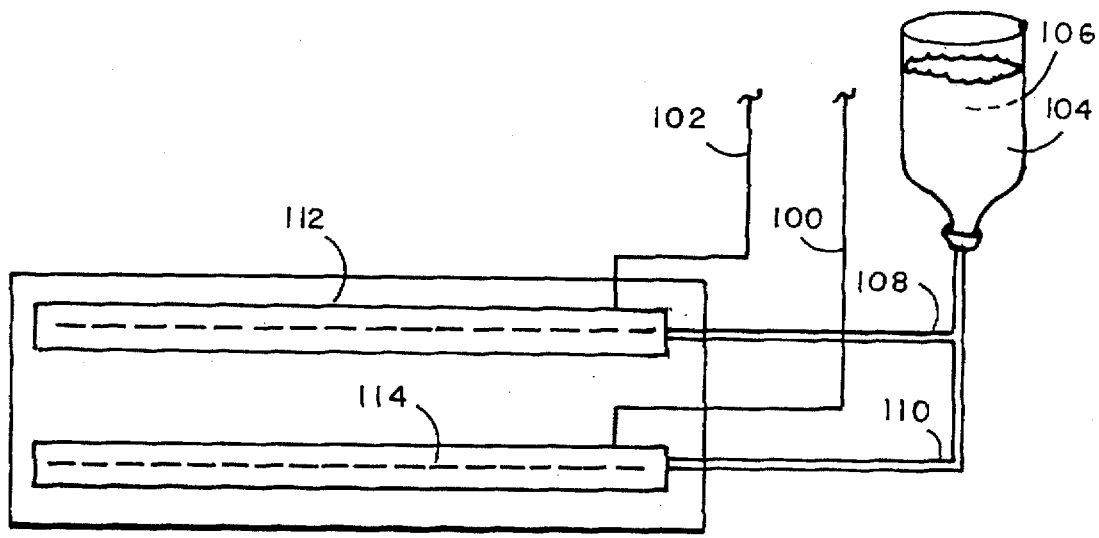
FIG. 8 illustrates a side view of an electrophoretic pharmaceutical titration delivery system having a fluid reservoir connected to the apparatus.

Another aspect of this invention concerns the transdermal electrophoretic pharmaceutical delivery system. The purpose of electrophoresis is to utilize an electrical field to influence the transfer and metabolism of the drug medium into the patient's body. FIG. 8 illustrates a side view of a drug 104 in a container 106 delivered along pipes 108 and 110 to controlled delivery valves 112 and 114 which can be placed within the tub. Electric lines 100 and 102 run from the console where they control the opening and closing of valves 112 and 114 to selectively allow drug 104 to enter tub 10. This drug entry device can use computer controlled titration and have sensors in the fluid medium to sense the amount of unabsorbed drug and adjust the rate of drug delivery to maintain the optimum concentration level. To aid in this purpose, stimulator electrodes 70 are arranged around the tub to allow for electrical continuity and provide homogenous flow of electrotherapeutic current within the bath solution. The electric field thereby flows in contact with, and around, the area of the patient's body being treated. It should be further noted that selected stimulator electrodes 70 can be oppositely charged, being energized by pulse signal generator 64b through the respective conductor lines, such as 72 and 73, and that each of electrodes 70 will at all times be in contact with the fluid medium in the tub. The application of the electrical current in a fluid medium provides an ionization effect producing a more effective delivery path to the patient. The method described herein is particularly advantageous to provide a path of consistent and continuous drug delivery around a body part.

A water hose link-up 22 to tub 10 is available for hook up directly to an outside water source to fill the tub with water. Thermal effects can be used from either hot or cold water which water can be supplied from an outside water source. A temperature gauge can be attached to the bath for measuring the temperature of the fluid in Celsius or Fahrenheit degrees. A heater can be utilized to maintain the fluid temperature at a constant desired level. It is well known that temperature can influence transdermal transport of drugs during the iontophoresis process.

Figure 6:
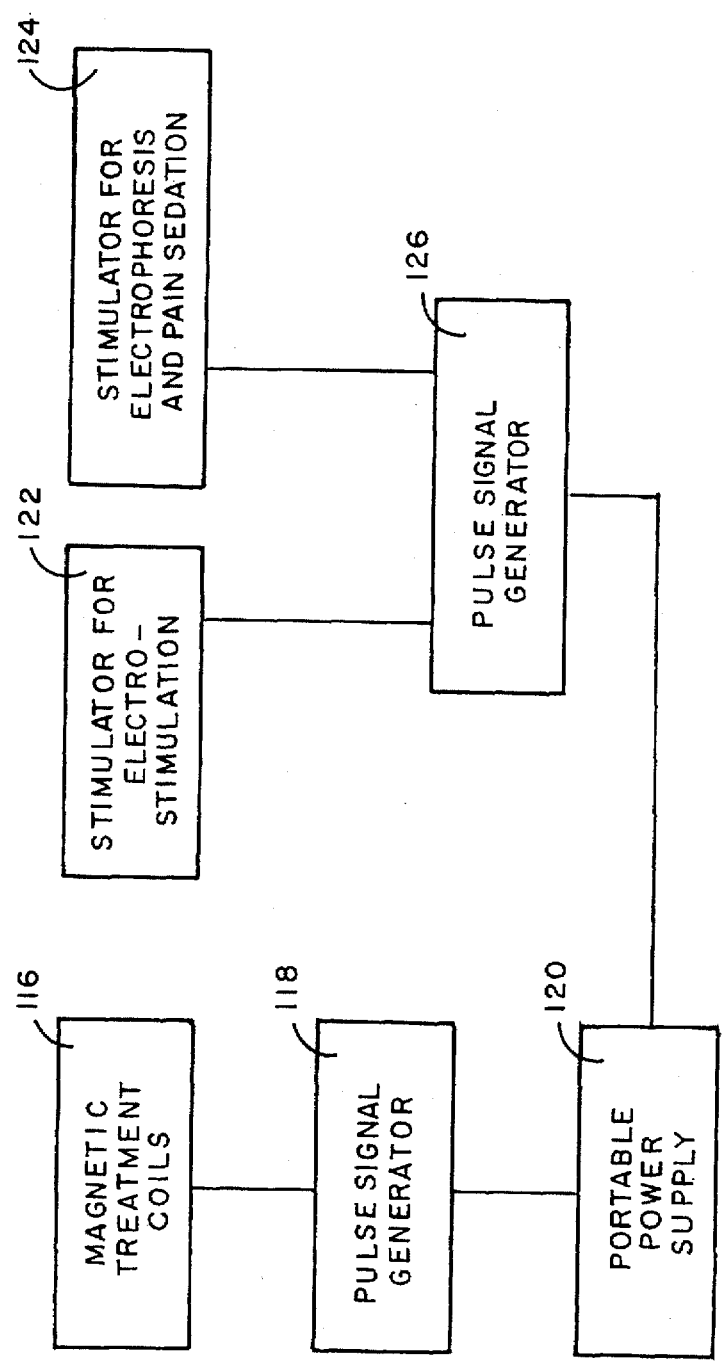
FIG. 6 illustrates a block diagram of the circuits of this invention divided into convenient functional sections.

It should be apparent that a clinician can choose options of desired therapy singly or in combination using operating console 20. FIG. 6 illustrates a schematic view of block diagrams of the circuitry of the device of this invention showing power supply 120 directing current through first pulse signal generator 118 and second pulse signal generator 126. First pulse signal generator 118 drives magnetic treatment coils 116, and second pulse signal generator 126 drives stimulator for electrostimulation 122 and stimulator for electrophoresis and pain sedation 124. A microprocessor with a sensor read-out can be provided that measures impedance in the skin, muscle and fat tissues to assist the clinician in adjusting the level of therapy energy to be applied to the patient.

Although the present invention has been described with reference to particular embodiments, it will be apparent to those skilled in the art that variations and modifications can be substituted therefor without departing from the principles and spirit of the invention.

I claim:

1. A submersive therapy apparatus comprising:

a tub having a floor, sides and an inner lining;

an aqueous solution disposed within said tub;

a multiple arrangement of electrodes housed around said sides and floor of said inner lining of said tub, said tub being of various shapes and sizes;

an electrotherapy device for providing alternating positive and negative currents to said electrodes to be used in contact with said aqueous solution for physiotherapy or iontophoresis treatment;

an ultrasound device for providing ultrasound treatment by an array of multiple ultrasound treatment heads disposed around said sides and floor of said inner lining of said tub, a magnetotherapy device for providing magnetotherapy by an array of magnetotherapy coils contained within said sides of said tub;

said apparatus characterized by being versatile and compatible with commercially available ultrasound and electrotherapy stimulation devices, said apparatus further including means for connecting an adapter console with a male or female jack adapter to accommodate said commercially available ultrasound and said commercially available electrotherapy stimulation devices for the providing of physiotherapy and enhanced drug delivery depth penetration by physical stimulation and acceleration of metabolic absorption resulting from enhanced membrane permeability of a patient's skin by acoustic, electrical, or electromagnetic energies.

2. The apparatus of claim 1 wherein said console can include an acoustic, electrical and/or electromagnetic power sources built therein to supply power directly to said apparatus.

3. A submersive therapy apparatus comprising:

a tub having a floor, sides and an inner lining;

an aqueous solution disposed within said tub;

a multiple arrangement of electrodes housed around said sides and floor of said inner lining of said tub, said tub being of various shapes and sizes;

an electrotherapy device for providing alternating positive and negative currents to said electrodes to be used in contact with said aqueous solution for physiotherapy or iontophoresis treatment;

an ultrasound device for providing ultrasound treatment by an array of multiple ultrasound treatment heads disposed around said sides and floor of said inner lining of said tub, a magnetotherapy device for providing magnetotherapy by an array of magnetotherapy coils contained within said sides of said tub;

said apparatus further including a microprocessor having a sensor read-out that measures impedance in a patient's skin, muscle, and fat tissues to assist a clinician in adjusting the necessary energy to be applied to said patient.

4. The apparatus of claim 3 further including an electromagnetic field in combination with a drug disposed in said aqueous solution to produce electro-magnetophoresis.

5. A submersive therapy apparatus comprising:

a tub having a floor, casing walls and an inner lining:

a fluid medium disposed within said tub;

an array of magnetotherapy coils for generating a magnetic field when energized, said magnetotherapy coils contained within said casing walls of said tub with said magnetotherapy coils positioned perpendicularly with respect to a target area defined within said tub, said magnetotherapy coils consecutively distributed within said casing wall for simultaneously generating an electromagnetic field in said fluid medium;

wherein said casing walls of said tub are composed of a magnetic shielding substrate material or composite material to create a "rebound effect" off said casing walls to increase the continuity of the magnetic field aimed toward a body treatment target area defined in said tub; and further including a microprocessor having a sensor read-out that measures impedance in a patient's skin, muscle and fat tissues to assist a clinician in adjusting the necessary energy to be applied to said patient.

6. The apparatus of claim 5 further including with said electromagnetic field a drug disposed in said fluid medium to produce electro-magnetophoresis.

7. A submersive therapy apparatus comprising:

a tub having a floor, sides and an inner lining;

an aqueous solution disposed within said tub;

an array of multiple, movable ultrasound treatment heads disposed around said sides and floor of said inner lining of said tub, said tub being of various shapes and sizes, said ultrasound heads focusable at a desired angle and in contact with said aqueous solution;

means for providing ultrasonic energy to said ultrasound treatment heads; and means for using at least one ultrasound and drug delivery treatment regimen as desired to an injured or diseased body member, said apparatus characterized by being versatile and compatible with commercially available ultrasound devices, said apparatus further including means for connecting an adapter console with male or female jack adapter to accommodate said commercially available ultrasound stimulation devices for the delivery of physiotherapy by acoustic energy.

* * * * *